Figure 1:
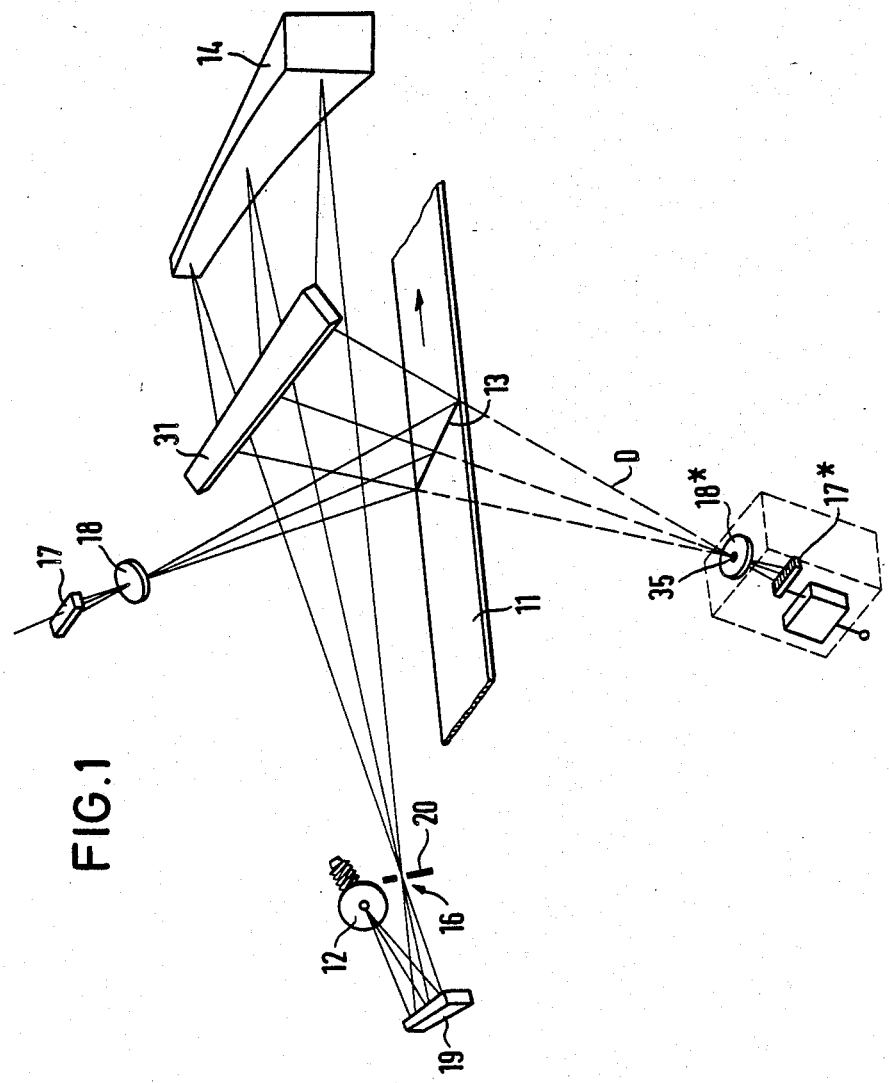

United States Patent [19]

Weber

[11] Patent Number: 4,938,601
[45] Date of Patent: * Jul. 3, 1990

[54] OPTICAL WEB MONITORING DEVICE WITH ROW CAMERAS WITH DIRECTED ILLUMINATION

[75] Inventor: Klaus Weber, Königsbronn, Fed. Rep. of Germany

[73] Assignee: Erwin Sick GmbH Optik-Elektronik, Waldkirch, Fed. Rep. of Germany

[*] Notice: The portion of the term of this patent subsequent to Oct. 4, 2005 has been disclaimed.

[21] Appl. No.: 169,704

[22] Filed: Mar. 18, 1988

[30] Foreign Application Priority Data

Mar. 23, 1987 [DE] Fed. Rep. of Germany ....... 3709500

[51] Int. Cl.⁵ ...................... G01N 21/86; G01N 21/89
[52] U.S. Cl. ..................................... 356/429; 250/572; 356/431
[58] Field of Search .............. 356/237, 376, 426, 429, 356/430, 431; 250/561, 562, 563, 571, 572; 358/106

[56] References Cited

U.S. PATENT DOCUMENTS 2,548,551 4/1951 Morrison ............................. 356/237
4,664,520 5/1987 Matsuo et al. .................. 250/563 X
4,775,238 10/1988 Weber ............................. 250/563 X

FOREIGN PATENT DOCUMENTS

| 0123929 | 3/1984 | European Pat. Off. . |
| 2100304 | 7/1971 | Fed. Rep. of Germany . |
| 2152510 | 4/1972 | Fed. Rep. of Germany . |
| 2827704 | 1/1980 | Fed. Rep. of Germany . |
| 3013244 | 10/1980 | Fed. Rep. of Germany . |
| 2925734 | 1/1981 | Fed. Rep. of Germany . |
| 8328870 | 1/1984 | Fed. Rep. of Germany . |
| 3304817 | 8/1984 | Fed. Rep. of Germany . |
| 3534018 | 4/1987 | Fed. Rep. of Germany . |

Primary Examiner—Vincent P. McGraw
Attorney, Agent, or Firm—Townsend and Townsend

[57] ABSTRACT

An optical web monitoring device is described for which a directed illumination is realized by means of a mirror strip which fully illuminates the pupil of the camera objective of a diode row camera with the image of the illuminating pupil. All contrasting methods can thus be used also for the finding of surface faults in running webs. Several cameras or one camera with pupil division and two diode rows can be simultaneously illuminated using one illuminating device.

13 Claims, 5 Drawing Sheets

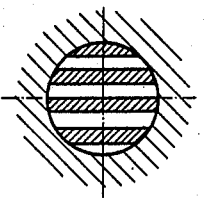
FIG. 2(1)  BP16
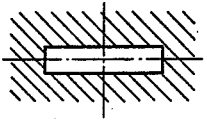
FIG. 2(2)
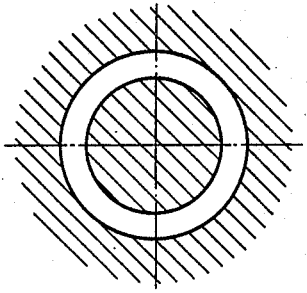
FIG. 2(3)
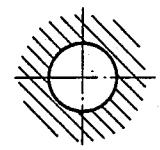
FIG. 2(4)
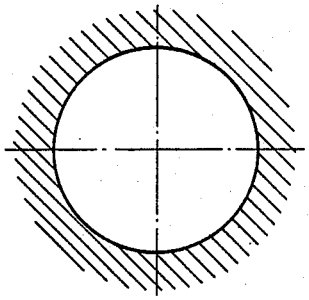
FIG. 2(5)
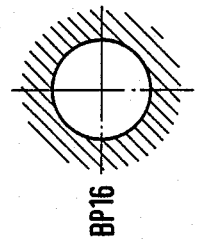
FIG. 2(6)
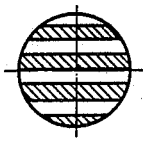
FIG. 2(7)  OP18
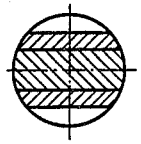
FIG. 2(8)
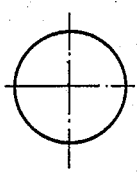
FIG. 2(9)
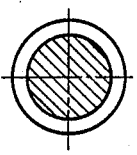
FIG. 2(10)
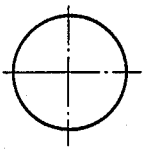
FIG. 2(11)
FIG. 2(12)

FIG. 5(1)
FIG. 5(2)
FIG. 5(3)
BP
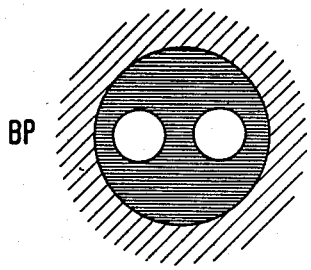
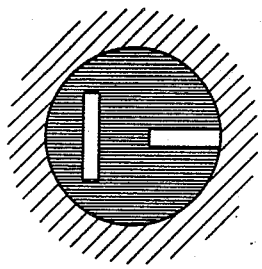
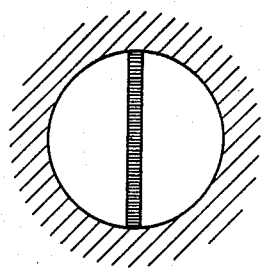
FIG. 5(4)
FIG. 5(5)
FIG. 5(6)
OP
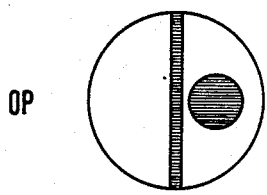
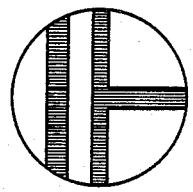
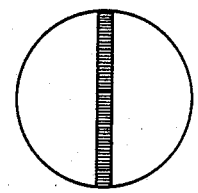

OPTICAL WEB MONITORING DEVICE WITH ROW CAMERAS WITH DIRECTED ILLUMINATION

The present invention relates to an optical web monitoring device with diode row cameras as sensor and indeed especially to the illuminating and contrasting devices thereof. The present invention is concerned with a further development of the invention described in the copending U.S. Patent Application Ser. No. 900 755, the content of which is fully incorporated herein by reference.

It is necessary to distinguish between two cases having regard to the optical characteristics of the material and the purpose for which the material is being monitored.

Case 1 relates to the search for faults on strongly scattering material such as paper and textiles. In this case the strip imaged by the camera transverse to the material web is intensively illuminated by one or more lamps in order to obtain a strength of illumination which is as high as possible. This high strength of illumination makes the material strip which is imaged onto the diode row into a self-luminous source which generates the desired strength of illumination on the diode row in correspondence with the light strength of the camera objective. Only when this luminous strength is sufficiently high can the rows be read out with a frequency which is required for the web speeds which are customary today during production. The illuminating devices for such monitoring systems thus require lamps with input powers of up to a few kW per meter of web width.

Case 2 relates to the search for faults in non-scattering or only very weakly scattering materials such as clear foils, glass plates or smooth sheet metal, however also to the detection of holes, cracks and edge positions of materials of any desired surface. The illuminating device required for these monitoring tasks present a strip-like light source or a secondary source in the proximity of the material web, with the source being matched in length to the web width, and with the material strip which is imaged in transmission or reflection by the row camera appearing in front of this source as a background. The luminous intensity of this light source thus determines the strength of illumination which can be achieved through the camera objective on the diode row. Suitable light sources are fluorescent tubes because of their particularly uniform light intensity distribution (light intensity approximately 2 stilb). Milk glass or mat glass strips illuminated from the rear by incandescent lamps serve as secondary sources (luminous intensity up to a few hundred stilb). A secondary light source thus becomes more complicated the higher the required luminous intensity and the larger the width of the web to be monitored. In addition to this comes the fact that as a result of the geometry of the construction dark field illumination is only possible at angles of illumination perpendicular to the web strip being monitored, i.e. preferential directions must also be taken into account even during fault recognition.

The object of the present invention is to realise an illuminating and contrasting device for this second case, i.e. for the searching for faults on weakly scattering material webs and also to detect holes, tears and edge positions in any desired material, in which the indicated restrictions and deficiencies are avoided.

In order to satisfy this object the imaged material strip is so illuminated, in accordance with claim 1, that the pupil of the illuminating arrangement is imaged into the pupil of the observing objective of the diode row camera.

With this illuminating device one ensures, when the pupil of the observing objective is wholly filled out by the image of the illuminating pupil and this in turn is fully filled with the image of the light source, as explained further below, that the object for the camera appears as bright as if it had the luminous intensity of the light source. In the case of an incandescent halogen lamp one can achieve up to 2000 stilb in this way, in the case of a xenon high pressure lamp up to 20.000 stilb effective luminous intensity of the object, i.e. at least one and up to two orders of magnitude more than with the brightest commercial illuminating systems.

In the special embodiment of claim 2 a strip-like spherical concave mirror is used as the single element for the imaging of the diaphragm, the spherical concave mirror entirely free of imaging faults for imaging scales at the level of approximately 1:1. That signifies that the fault-free image of the illuminating diaphragm in the pupil of the camera objective is fully covered over, for example for dark field observation of a complementary diaphragm in accordance with claim 3 which is of only fractionally larger dimensions. Even small deflections of the illuminating beam due to irregularities in the object will thus lead to increases in brightness on the diode row which can be registered as fault signals. In comparison to the previous arrangements the sensitivity is not only considerably increased but also any form of preferential direction is also avoided.

In general all optical contrasting methods (contrast entrancing methods) which are helpful for detecting faults on material webs in reflection or transmission can be realised in conjunction with the directed illumination through suitable diaphragm combinations.

When expedient for the distinguishing of faults two row cameras can also be simultaneously operated with the same illuminating device: one camera in transmission indicates holes in a non-transparent foil in the bright field whereas the other camera indicates bumps, folds or pitting in reflection in the dark field. If geometrical structures on the material webs are to be detected then it is often necessary to execute the directed illumination and the associated camera telecentrically in accordance with claim 4. This telecentric illuminating and observing web monitoring device detects in fault-free manner the dimensions of the structure to be monitored, even with a small degree of defocussing brought about by unevenness. All contrast processes can also be realised here.

One can extend the possibilities of the previously described devices if in accordance with claims 5 to 8, one provides the camera with pupil division, allows each half of the pupil to precisely image the same strip of the material web onto a respective diode row, and forms an image of two illuminating pupils on the two pupil halves with one and the same illuminating device.

In such a system with directed illumination and a double camera with pupil division, provision is expediently made that both diode rows can be synchronously read out so that two pieces of information are simultaneously obtained for each object point. Depending on the requirement one selects for this purpose to supplementary contrasting methods for the two pupil halves.

Naturally a pair of congruently aligned row cameras can also be used, starting from one illumination pupil, via a dividing mirror if, for example, only light field and inner dark field contrasting is to be realised, which both require the same illumination diaphragm.

Two directly adjacent row cameras which are aligned onto the same line on the material web can also be supplied by a common illumination device if two illuminating pupils with a corresponding spacing are provided.

In the following embodiments of the invention are illustrated in the figures and described. The figures show:

FIG. 1 Row cameras with directed illumination, an arrangement in accordance with the application P 35 34 019.52.

FIG. 2 Diaphragm configurations for contrasting processes with a row camera with directed illumination, with BP signifying the illumination pupil and OP the objective pupil.

Figure 3:
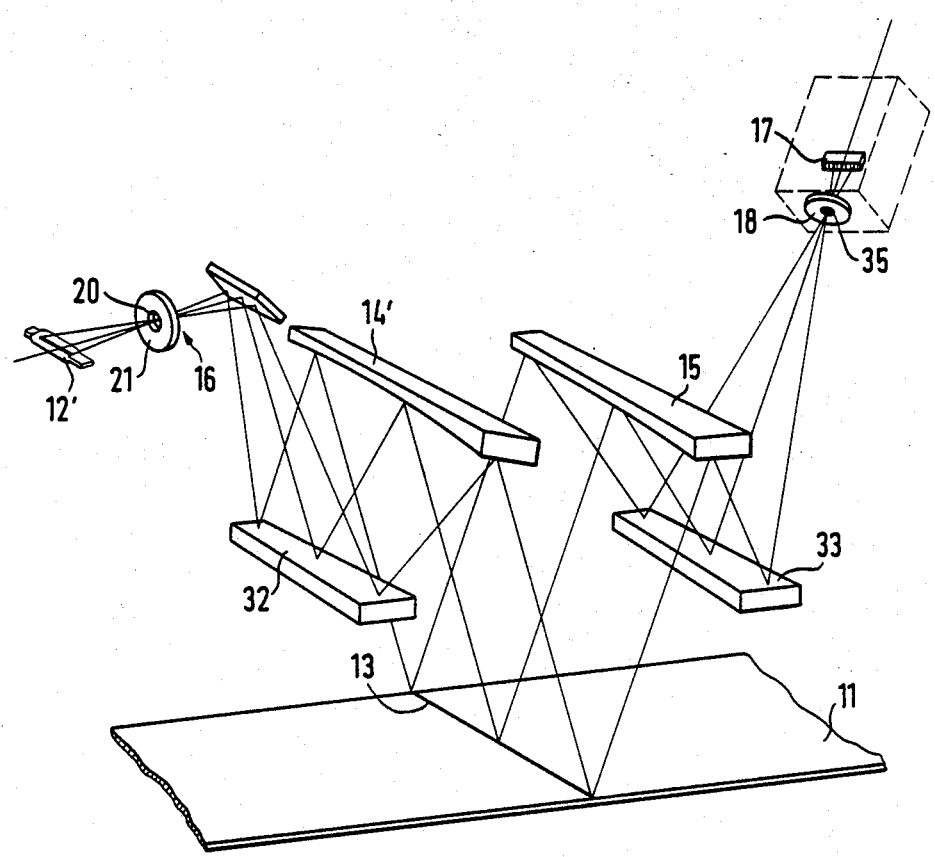

FIG. 3 Row camera with directed telecentric illumination and telecentric imaging row camera.

Figure 4:
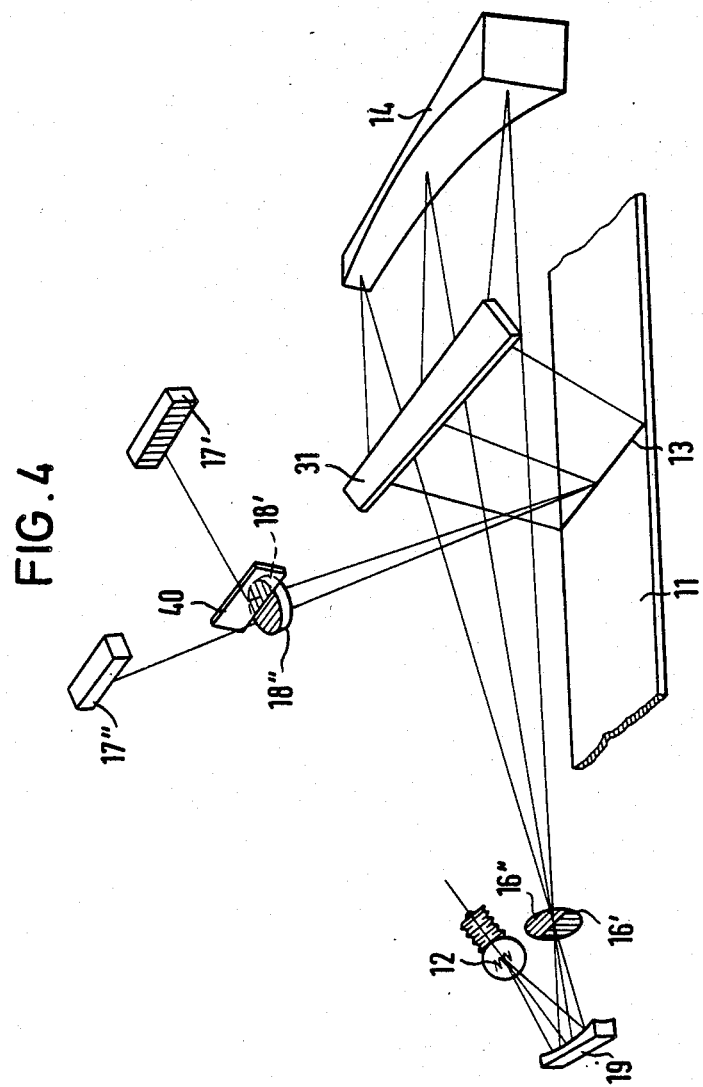

FIG. 4 Row camera with divided pupil and two congruent diode rows with directed illumination with correspondingly divided illumination pupils.

FIG. 5 Diaphragm configurations for contrasting processes for a camera with divided pupils and two congruent diode rows with directed illumination with correspondingly divided pupils.

FIG. 1 illustrates a convergent directed illumination arrangement for row cameras as described in the main patent. The light source 12 illuminates the diaphragm 20 via the collector mirror strip 19 with the diaphragm 20 forming the illumination pupil 16. This illumination pupil lies at the centre of curvature of the concave mirror strip 14 and is thus imaged by the latter in the scale 1:1 via the plane deflecting mirror strip 31 and the surface of the material web 11 in transmission into the pupil of the camera objective 18* of the row camera for checking in transmission, and is imaged in reflection at the surface 11 into the pupil of the camera objective 18 of the row camera for checking in reflection. The camera objectives in turn form an image of the illuminated material strip 13 in each case on the diode row 17* and 17 respectively. Only the very narrow part of the illuminated material strip whose image is picked up by the diodes of the row contributes, after photoelectric conversion and read-out of the electrical signals, to information concerning the surface along this small quasi linear region within the illuminated strip 13. Through the exact imaging of the illumination pupil 16 into the pupil of the camera objective 18, 18* it is possible to realise a series of contrasting processes in which suitable diaphragms matched to one another are inserted into the two pupils. A series of such diaphragm configurations is shown in FIG. 2 in which the diaphragm arranged in the illuminating pupil 16 is shown in the upper row and the corresponding diaphragm arranged in the objective pupil 18 is reproduced in the lower row.

In detail the following configurations result:

No. 1 Light field (The image of the illuminating diaphragm lies in the observing diaphragm.), No. 2 Light field "overilluminated" (If the illuminating diaphragm is substantially larger than the observing diaphragm then object parts which are locally somewhat inclined will still be reproduced with the same brightness.), No. 3 Inner dark field (The image of the illuminating diaphragm is covered over by a central diaphragm in the observing objective. Only beam deflecting faults appear light.), No. 4 Outer dark field (The illuminating diaphragm is ring-shaped, the inner diameter of the ring is little larger than the selected objective diaphragm. Advantage over No. 3: no interference in the camera objective necessary, sensitivity can simply be selected by adjusting the iris diaphragm of the objective.), No. 5 Schlieren arrangement A (The illuminating diaphragm is a gap, is imaged onto a complementary non-transmitting strip in the objective pupil. Schlieren (e.g. effects due to changes in refractive index) with gradients perpendicular to the slot longitudinal direction are detected. Possible extension: light attenuating transition strips permit statements concerning the angle of deflection.), and No. 6 Schlieren arrangement B (As an illumination diaphragm a grid with impermeable (opaque) webs is imaged onto a complementary grid in the objective pupil which has narrower transmission strips. Even small gradients are made visible here, however the indicated deflection range is smaller.).

The arrangement shown in FIG. 3 of a row camera with directed illumination is telecentric both on the illumination side and also on the observing side. This is achieved in that the illuminating pupil 16 lies in the focal plane of the concave mirror strip 14', the illuminating beams thus impinge onto the material surface 11 at the illuminated strip 13 at the same angle over the entire length. On the observing side the pupil of the camera objective 18 is arranged in the focal plane of the concave mirror strip 15, so that the image forming beams are likewise telecentric. As an example for the type of contrasting an inner dark field is selected which can be recognised from the central diaphragm 35. A further special feature here is the illumination of the illuminating pupil 16 with its diaphragm 20: As an example a light source 12' with a long narrow filament is selected here and is imaged in enlarged manner into the material surface 11 by a field lens 21 via a concave mirror strip 14' and the plane deflecting mirror strip 32. The light source, optionally blurred by suitable scattering means forms the illuminating strip 13 which is then in turn imaged by the camera objective onto the diode row 17 via the concave mirror strip 15 and the deflecting mirror strip 33. This arrangement of the illumination with imaging of the light source into the material surface is particularly advantageous when the light source is bar-like and has no structure, for example is formed by a combustive gas discharge in a capillary.

The arrangement shown in FIG. 4 is distinguished from that shown in FIG. 1 in that here the illuminating pupil is split up into two halves 16' and 16" with which two pupil halves 18' and 18" in the camera objective are associated. The deflecting mirror 40 is inserted directly behind the camera objective and extends up to the optical axis. It thus divides the image forming beam path to the two diode rows 17' and 17" in accordance with the two pupil halves and is so adjusted that congruent images of the same objective in the illuminated strip arise on both rows. The n diode of row 17' thus receives an image of the same position of the surface 11 as the n diode of the row 17".

If one now selects different contrast processes for the two pupil halves then one obtains two corresponding pieces of information for each object point.

FIG. 5 shows a selection of diaphragm configurations for contrasting processes for the cameras with divided pupils. The illuminating diaphragm pairs are shown in the upper row and the associated observing diaphragm pairs are shown in the lower row. The following configurations are expedient:

No. 1: Light field and inner dark field. In reflection flecks appear darker in the light field, holes appear black and in the dark field scratches and other unevenness appear light.

No. 2: Schlieren, split up in direction. Staged information concerning the angle of deflection is also possible here in the observing aperture halves through grey regions on the two sides of the beam diaphragm.

No. 3: Colour shifts. With suitable colour filters F 1, F 2 before the halves of the pupil one can detect colour shifts in the moving material.

Changes in direction of oscillation of polarised light or changes of fluorescent brightnesses can also be registered.

I claim:

1. Optical web monitoring device with a diode row camera, characterised in that the imaged material strip is illuminated by means of two strip-like optical image forming elements (14', 15) via deflecting mirrors (32, 33) in such a way that the illuminating pupil (16) is imaged into the pupil of the observing objective (18) and this illuminating beam path is telecentric at the location of the illuminated material strip, with the second strip-like optical image forming element (15) being arranged at the distance of its focal length from the pupil of the observing objective (18), so that the observing beam path is also telecentric.

2. Optical web monitoring device with a diode row camera and an objective pupil having two halves (18, 18'), said pupil halves each forming the image of one and the same strip (13) of the material web (11) on a linear arrangement of diodes (17, 17'), characterized in that the material strip (13) which is imaged is so illuminated by means of a strip-like concave mirror (14) that in each case one half of the pupil of an illuminating arrangement having two halves (16, 16') is imaged into a respective pupil half of the observing objective (18, 18'), said illuminating pupil halves (16, 16') having means for permitting two different contrasting methods to be simultaneously used with a common beam path from the illuminating pupil (16, 16') to the objective pupil (18, 18').

3. Device in accordance with claim 2, characterised in that two different contrast methods are selectively realised in each case through the use of suitable aperture stops in the halves (16, 16') of the illuminating pupil and in the pupil halves of the observing objective (18, 18').

4. Device in accordance with claim 2, characterised in that the pupil of the observing objective (18) is subdivided by a prism wedge which covers over half of the pupil.

5. Device in accordance with claim 2, characterised in that the pupils of the observing objective are divided by a deflecting mirror (40) arranged directly behind the objective and extending up to the optical axis.

6. Optical web monitoring device with two diode row cameras arranged directly alongside one another through which one and the same strip (13) of the material web (11) is imaged onto a diode row in each case, characterised in that the imaged material strip is so illuminated by means of a strip-like spherical concave mirror (19) that a pair of pupils of the illuminating arrangement (16, 16A) matched to the pair of pupils of the observing objective (18, 18A) is imaged into the latter.

7. An optical web monitoring apparatus comprising:
    illumination means for generating a strip of illumination on a surface of a web, said illumination means comprising a light source, an illumination pupil having a selectable aperture stop, and a strip-like image forming element illuminated by the light source; and
    a light receiving arrangement comprising an optical system, a camera objective pupil having a selectable aperture stop, a photoreceiver arrangement formed by a line of diodes, and an electronic processing circuit,
    said light receiving arrangement projecting light emerging from the strip of illumination via said optical system onto said photoreceiver arrangement which delivers electrical signals corresponding to the received light to said electronic processing circuit,
    said image forming element forming an image of the illumination pupil onto the camera objective pupil.

8. The apparatus of claim 7 wherein the illumination pupil aperture stop and the camera objective pupil aperture stop are selected to produce bright field contrast.

9. The apparatus of claim 7 wherein the illumination pupil aperture stop and the camera objective pupil aperture stop are selected to produce inner dark field contrast.

10. The apparatus of claim 7 wherein the illumination pupil aperture stop and the camera objective pupil aperture stop are selected to produce outer dark field contrast.

11. The apparatus of claim 7 wherein the illumination pupil aperture stop and the camera objective pupil aperture stop are selected to produce Schlieren contrast.

12. The apparatus of claim 7 wherein the illumination pupil aperture stop and the camera objective pupil aperture stop are selected to produce phase contrast.

13. Device in accordance with claim 7, characterised in that the imaging of the illuminating pupil (16) into the pupil of the observing objective (18) takes place with a strip-like spherical concave mirror (14) in conjunction with a plane deflecting mirror (31) approximately to an imaging scale of 1:1.

* * * * *